(12) United States Patent
Moore et al.

(10) Patent No.: US 7,578,820 B2
(45) Date of Patent: Aug. 25, 2009

(54) DEVICES AND TECHNIQUES FOR A MINIMALLY INVASIVE DISC SPACE PREPARATION AND IMPLANT INSERTION

(76) Inventors: Jeffrey D. Moore, 6191 Ivy Trails Dr., Oliv Branch, MS (US) 38654; James P. Duncan, 9503 Bethel Rd., Olive Branch, MS (US) 38651; Jeffrey L. Scifert, 6764 Hare Run La., Arlington, TN (US) 38002; Charles L. Branch, 177 Plantation La., Advance, NC (US) 27006; Kevin T. Foley, 2877 Keasler Cir. West, Germantown, TN (US) 38139

( * ) Notice: Subject to any disclaimer, the term of this patent is extended or adjusted under 35 U.S.C. 154(b) by 1088 days.

(21) Appl. No.: 10/653,281

(22) Filed: Sep. 2, 2003

(65) Prior Publication Data
US 2005/0049623 A1    Mar. 3, 2005

(51) Int. Cl.
*A61B 17/16* (2006.01)
(52) U.S. Cl. ......................... 606/84; 600/203
(58) Field of Classification Search .................. 606/79, 606/80, 84, 85, 96
See application file for complete search history.

(56) References Cited

U.S. PATENT DOCUMENTS

| | | | |
|---|---|---|---|
| 2,235,419 A | 3/1941 | Callahan et al. | |
| 2,878,809 A | 3/1959 | Treace | |
| 3,467,100 A | 9/1969 | Rubin | |
| 4,541,423 A | 9/1985 | Barber | |
| 5,312,407 A | 5/1994 | Carter | |
| 5,586,989 A | 12/1996 | Bray, Jr. | |
| 5,620,458 A * | 4/1997 | Green et al. | 606/188 |
| 5,785,647 A * | 7/1998 | Tompkins et al. | 600/201 |
| 5,836,958 A | 11/1998 | Ralph | |
| 6,059,829 A | 5/2000 | Schlapfer et al. | |
| 6,174,311 B1 | 1/2001 | Branch et al. | |
| 6,241,729 B1 | 6/2001 | Estes et al. | |
| 6,425,859 B1 | 7/2002 | Foley et al. | |
| 6,506,151 B2 | 1/2003 | Estes et al. | |
| 6,575,899 B1 | 6/2003 | Foley et al. | |
| 2002/0019637 A1 | 2/2002 | Frey et al. | |
| 2002/0068941 A1 | 6/2002 | Hanson et al. | |
| 2002/0165550 A1 | 11/2002 | Frey et al. | |
| 2003/0045880 A1 | 3/2003 | Michelson | |
| 2003/0216744 A1 | 11/2003 | Longhini et al. | |

FOREIGN PATENT DOCUMENTS

FR    2 769 827 A1    4/1999

* cited by examiner

*Primary Examiner*—Eduardo C Robert
*Assistant Examiner*—David Comstock (57) ABSTRACT

Methods and instruments are provided for performing spinal disc space preparation and implant insertion in minimally invasive procedures. The instruments include cutting instruments and implant insertion instruments adapted for insertion through a minimally invasive access portal to a spinal disc space. The proximal portions of the instruments are adapted to facilitate viewing through a proximal end opening of the access portal with the instruments positioned through the access portal while also enhancing the surgeon's control of the distal working end of the instruments while in the disc space.

16 Claims, 5 Drawing Sheets

DEVICES AND TECHNIQUES FOR A MINIMALLY INVASIVE DISC SPACE PREPARATION AND IMPLANT INSERTION

BACKGROUND

Access to a spinal disc space may be accomplished from several approaches to the spine, including anterior, posterior, anterior-oblique, lateral, and postero-lateral approaches. A sleeve or cannula can be employed in such approaches to provide a protected pathway to the spinal disc space, and to retract tissue, nerves, vasculature and other anatomical structures. The use of a sleeve, cannula or other portal minimizes tissue retraction and the trauma associated with open, invasive surgical techniques for accessing a spinal disc space. However, visualization of the operative site through the portal can be obstructed by the proximal portions of instruments employed in such procedures. Also, the proximal portions can be oriented relative to the distal working ends such that the gesturing required to manipulate the distal working end in the disc space with the shaft through the portal is cumbersome and/or does not facilitate the delivery of desired or needed working forces to the distal working end.

SUMMARY

The present invention relates to instruments and techniques for use in minimally invasive surgical procedures. More specifically, but not exclusively, the present invention relates to methods and instruments to facilitate minimally invasive disc space preparation and implant insertion.

According to one aspect, instruments are provided to prepare a spinal disc space for implant insertion and for inserting implants in a spinal disc space. The instruments include a distal working end and an elongate member including a proximal handle portion configured to facilitate viewing through a proximal end opening of an access portal and also to enhance control of the distal working end through a minimally invasive access portal.

In one aspect, a rotary cutting instrument is provided.

In another aspect, a scraper instrument is provided.

In further aspect, a chisel instrument is provided.

In still a further aspect, an implant insertion instrument is provided.

In yet another aspect, a method for spinal disc space preparation in a minimally invasive surgical approach and for implant insertion in a minimally invasive surgical approach is provided.

These and further aspects shall be apparent from the detailed drawings and descriptions provided herein.

DETAILED DESCRIPTION OF THE ILLUSTRATED EMBODIMENTS

For the purposes of promoting an understanding of the principles of the present invention, reference will now be made to the embodiments illustrated in the drawings, and specific language will be used to describe the same. It will nevertheless be understood that no limitation of the scope of the invention is intended thereby. Any alterations and further modification in the described processes, systems, or devices, and any further applications of the principles of the invention as described herein are contemplated as would normally occur to one skilled in the art to which the invention relates.

The instruments and techniques of the present invention provide for improved disc space preparation and implant insertion through a minimally invasive access portal. Cutting instruments and implants inserters are adapted for positioning through an access portal for controlled manipulation therethrough and further adapted to facilitate visualization of the surgical site through the proximal end opening of the access portal. The cutting instruments can be employed to prepare the intervertebral space between adjacent vertebrae for receiving an implant. Specific cutting instruments include rotary cutters, scrapers and chisels.

Figure 1:
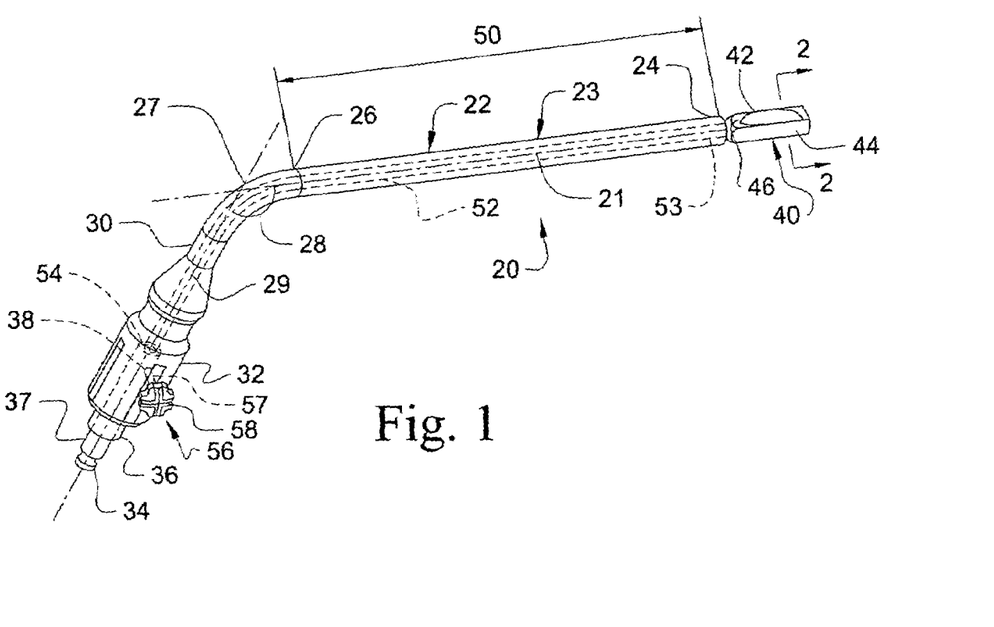
FIG. 1 is a perspective view of a rotary cutting instrument.

In FIG. 1 there is shown a rotary cutter 20 to remove disc and bone material through a minimally invasive access portal. Rotary cutter 20 includes a rigid elongate member 22 and a rotary cutting element 40 extending distally from and rotatably mounted to elongate member 22. Elongate member 22 is hollow to receive an inner shaft 52 therethrough. Elongate member 22 includes a linear distal shaft portion 23 extending between a distal end 24 and a proximal end 26 along a distal longitudinal axis 21. Distal shaft portion 23 includes a length 50 between distal end 24 and proximal end 26. A lateral bend 27 extends proximally from proximal end 26 to a proximal shaft portion 30. Proximal shaft portion 30 extends along a proximal longitudinal axis 29, and is coupled to a handle 32 extending proximally therefrom to facilitate manual gripping of rotary cutter 20.

Proximal longitudinal axis 29 forms an angle 28 with distal longitudinal axis portion 21. Angle 28 offsets handle 32 and any tools engaged to the proximal end of instrument 20 away from distal longitudinal axis 23. In one embodiment, angle 28 is 150 degrees. In another embodiment, angle 28 ranges from 135 degrees to about 165 degrees. In yet another embodiment, angle 28 ranges from 90 degree to 150 degrees.

A flexible inner shaft 52 extends through proximal shaft portion 30, lateral bend 27 and distal shaft portion 23. The flexible inner shaft 52 can be made from, for example, cable, stainless steel coiled wire or nitinol. The distal end 53 of flexible inner shaft 52 is coupled to rotary cutting element 40. The proximal end 54 of flexible inner shaft 52 is coupled to a proximal inner shaft portion 37. Proximal inner shaft portion 37 extends through at least a portion of handle 32 and proximally therefrom to a tool engaging member 34 at its proximal end. Tool engaging member 34 can be, for example, Hudson type connector. A bearing shaft 36 rotatably couples proximal inner shaft portion 37 to the proximal end opening of handle 32. A manual handle, such as a T-handle, may be attached to drive tool engaging member 34 to effect a rotational force to inner shaft portion 37 and flexible inner shaft 52 to rotate cutting element 40. It is also contemplated that a power tool can be attached to drive tool engaging member 34 to deliver a rotary force to cutting element 40 through inner shaft 52.

Proximal inner shaft portion 37 can be rigid and include an outer groove 38 extending therearound. A coupling member 56 includes a pin 57 extending through and threadingly engaged with handle 32, with a distal end portion of pin 57 positioned in groove 38. A hand knob 58 positioned along handle 32 allows pin 57 to be withdrawn from groove 38 for rapid disassembly of the inner and outer shafts to facilitate cleaning of instrument 20.

Figure 2:
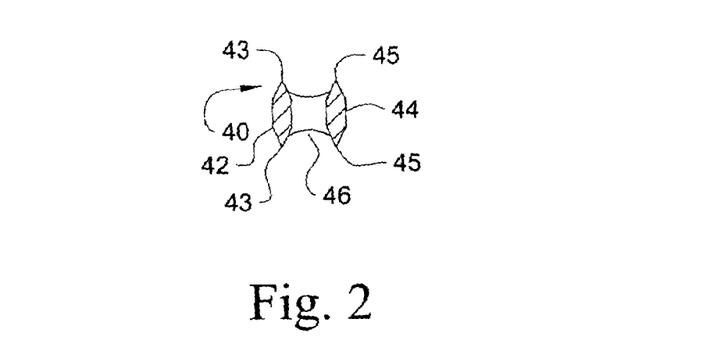
FIG. 2 is a section view through line 2-2 of FIG. 1.

As further shown in FIG. 2, rotary cutting element 40 includes a first cutting arm 42 and a second cutting arm 44 extending generally parallel with one another in the direction of distal longitudinal axis 23. First cutting arm 42 and second cutting arm 44 are spaced apart from one another and define a chamber 46 therebetween for receipt of cutting debris. First cutting arm 42 includes at least one cutting blade 43 extending therealong at the upper and lower sides thereof. The outer surfaces of first cutting arm 42 can include convexly curved surface profiles between the upper and lower cutting blades 43. Similarly, second cutting arm 44 includes at least one cutting blade 45 along the upper and lower sides thereof. The outer surfaces of second cutting arm 44 can include convexly curved surface profiles between the upper and lower cutting blades 45. The cutting blades 43, 45 extend longitudinally and are positioned to lie parallel to the longitudinal axis 21 of distal shaft portion 23. Cutting element 40 may be moved to various locations in the disc space by manipulating elongate member 22 and cutting element 40 with handle 32 for removal of disc material, cartilage, or other tissue to form a channel for insertion of an implant.

Figure 3:
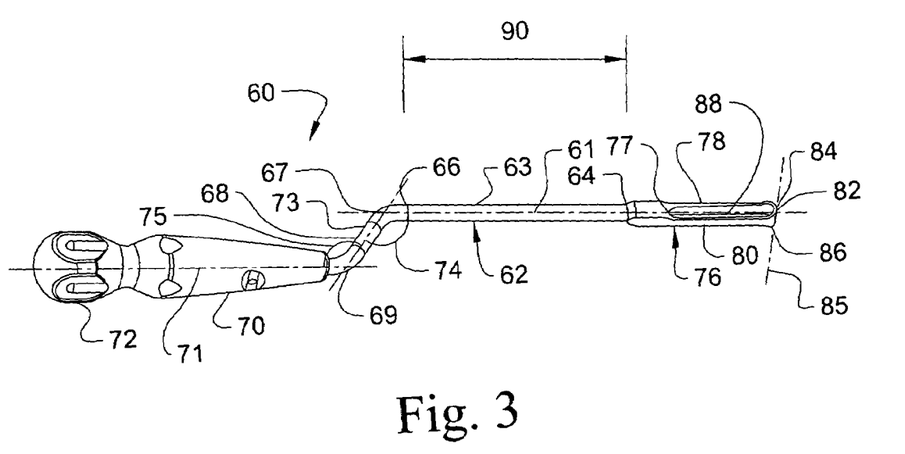
FIG. 3 is a perspective view of a scraper instrument.

Referring to FIG. 3, there is shown a scraper 60 to prepare a disc space through a minimally invasive access portal. Scraper 60 includes a rigid elongate member 62 with a cutting element extending axially from a distal end 64. Elongate member 62 includes a distal linear shaft portion 63 extending along a longitudinal axis 61. Distal shaft portion 63 includes a length 90 extending between distal end 64 and a proximal end 66. A first lateral bend 67 extends proximally from proximal end 66 of distal shaft portion 62. An offset shaft portion 68 extends along an offset axis 73 from first lateral bend 67 to a second lateral bend 69. A proximal linear shaft portion 70 extends from second lateral bend 69 along a proximal longitudinal axis 71, and is coupled to a proximal handle 72. It is contemplated that distal longitudinal axis 61 extends parallel to proximal longitudinal axis 71. In this configuration, angles 74, 75 are the same, and range from 90 degrees to 150 degrees. In one specific embodiment, angles 74, 75 are 120 degrees.

The distal cutting element is in the form of a scraper head 76 attached to and extending distally from distal end 64 of distal shaft portion 63. Scraper head 76 includes a body 77 at a proximal end thereof connected with distal shaft portion 63, and first and second arms 78, 80 extending distally from body 77. The distal ends of arms 78, 80 are connected with a distal end wall 82 comprised of upper and lower cutting blades 84, 86. First and second arms 78, 80 form a trough 88 therebetween to receive disc, bone, tissue and other material scraped by upper and lower cutting blades 84, 86. Cutting blades 84, 86 can be rounded and include proximally-facing cutting edges, which can cut bone or other tissue as the scraper head 76 is moved proximally in the disc space.

Blades 84, 86 are bisected by an axis 85 extending orthogonally to and intersecting a distal extension of distal longitudinal axis 61. Offset portion 68 extends from distal shaft portion 63 to offset proximal shaft portion 70 and handle 72 to the same side of distal longitudinal axis 61 as one of the cutting blades 84, 86, such as lower cutting blade 86. Upper cutting blade 84 extends in a direction from distal longitudinal axis 61 opposite the offset of proximal shaft portion 70 and lower cutting blade 86 from distal longitudinal axis 61. Proximal longitudinal axis 71 lies in a plane extending through distal longitudinal axis 61 and axis 85. Thus, proximal shaft portion 70 is aligned in the up and down directions required to move scraper head 76 to embed or firmly engage blades 84, 86 with the adjacent vertebral endplate. This positioning of handle 72 and proximal shaft portion 70 relative to cutting blades 84, 86 facilitates the manual maintenance of such engagement as scraper head 76 is withdrawn proximally in the disc space in the direction along distal longitudinal axis 61.

Scraper blades 84, 86 can be spaced apart from one another to allow simultaneous cutting on opposing surfaces of adjacent vertebral bodies. Alternatively, the scraper blades 84, 86 can be employed alternately on the adjacent upper or lower endplate of the adjacent vertebral body without requiring rotation in or removal of scraper head 76 from the disc space. The surgeon can angle or reposition elongate member 62 through the access portal with handle 72 to engage a respective one of the blades 84, 86 to the adjacent upper or lower endplate. One or both of the arms 78, 80 can include index markings to indicate the depth scraper head 76 is inserted into the disc space.

Figure 4:
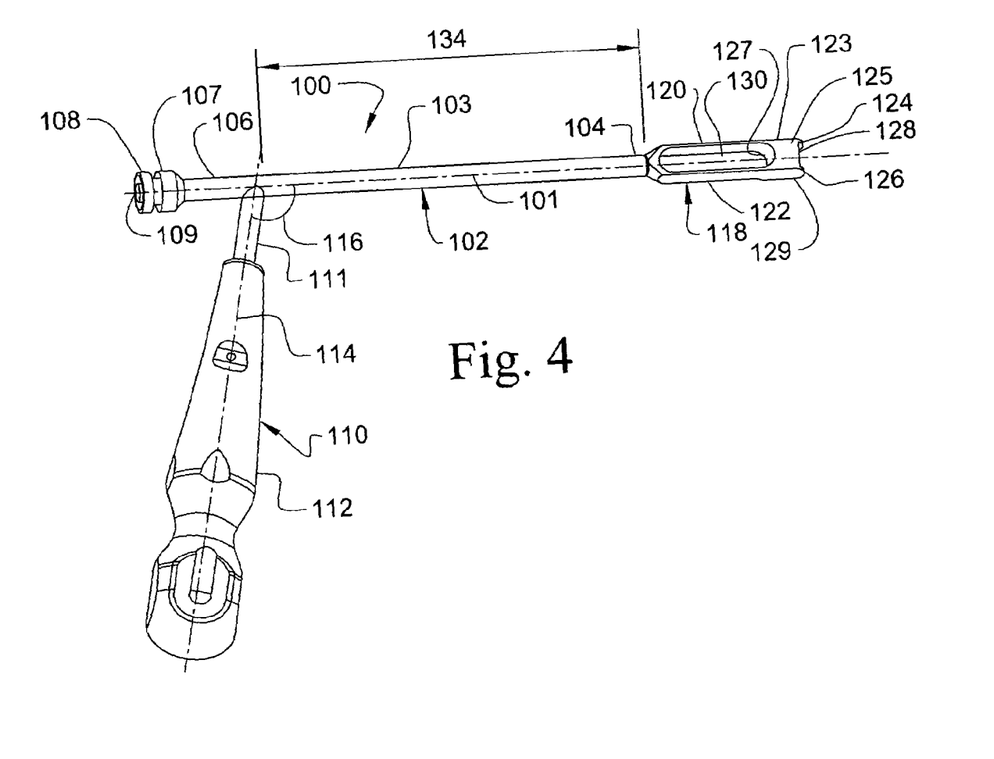
FIG. 4 is a perspective view of a chisel instrument.

In FIG. 4, a chisel 100 is provided to facilitate the preparation of a preformed cavity in the intervertebral disc space to receive an implant through a minimally invasive access portal. Chisel 100 includes an elongate member 102 in the form of a rigid, linear shaft having a distal portion 103 and a proximal portion 106. Elongate member 102 extends along a longitudinal axis 101, and includes a cutting element at a distal end 104 thereof. The proximal end 107 of elongate member 102 includes an impaction head 108 having a receptacle 109 to facilitate attachment of an impaction instrument, such as a slap hammer.

The distal cutting element includes a chisel head 118 including a first arm 120 and an opposite second arm 122 extending distally from elongate member 102 substantially parallel to longitudinal axis 101. A body 123 is provided at the distal ends of arms 120, 122, and includes a distal end opening between an upper cutting blade 128 and opposite lower cutting blade 129. Blades 128, 129 are disposed between first and second arms 120 and 122 along the distal ends of the upper and lower plates 125, 127 comprising body 123. Arms 120, 122 define an internal chamber 130 for receipt of bone chips and cutting debris removed by the upper and lower blades 128, 129 and deposited through the distal end opening of body 123 as chisel head 118 is distally advanced in the disc space. One or both of the arms 120, 122 can include index markings to indicate the distal penetration of chisel head 118 in the disc space.

A first distal extension 124 extends from first arm 120 distally beyond cutting blades 128, 129, and a second distal extension 126 extends from second arm 122 distally beyond cutting blades 128, 129. Extensions 124, 126 extend parallel to longitudinal axis 101. The upper and lower surfaces of distal extensions 124, 126 can contact the adjacent bony surfaces of the vertebral endplates on each side of the disc space to follow along the surfaces of the endplates and center the chisel head 118 and thus the cutting blades 128, 129 within the disc space. When the upper and lower cutting blades 128, 129 are centered between the opposing endplates, blades 128, 129 cut equal amounts of bone from each endplate and are prevented from creating a potential offset opening between the endplates. As a result, the implant can be properly positioned in the channel formed with chisel head 118 with reduced risk of improper implant placement, excess bone removal, and implant interface subsidence.

Chisel 100 further includes a handle member 110 extending transversely to elongate member 102 along an axis 114. Distal shaft portion 103 includes a length 134 between distal end 104 and the connection of handle member 110 with elongate member 102. Handle member 110 includes a shaft portion 111 and a handle 112 extending from shaft portion 111. Shaft portion 114 can be connected by being integrally formed with, welded or otherwise coupled to elongate member 102 to facilitate transmission of a manipulative force applied through handle 112 to the distal cutting element. Axis 114 of handle member 110 forms an angle 116 with axis 101 of elongate member 102 along distal portion 103. In one embodiment, angle 116 is 120 degrees. In its operative orientation, axis 114 lies in a plane extending parallel to and between upper and lower cutting blades 128, 129 and including longitudinal axis 101. This orientation facilitates the surgeon in manually manipulating the positioning and alignment of the distal cutting element laterally in the disc space, while an impaction force can be delivered simultaneously to impaction head 108 for transmission along elongate member 102 to longitudinal axis 101. The impaction force facilitates advancement of chisel head 118 distally in the disc space while lateral alignment is controlled with handle member 110.

Figures 5, 6:
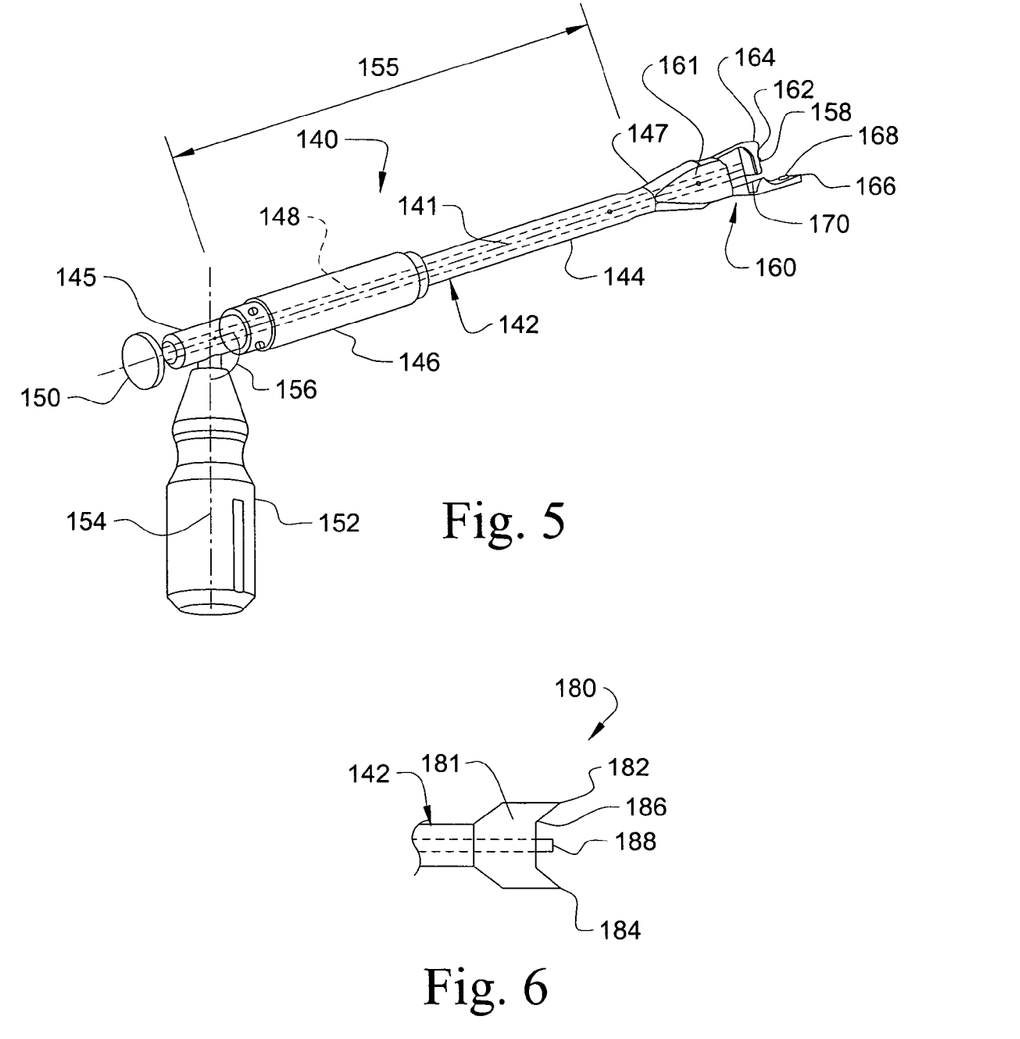
FIG. 5 is a perspective view of an implant inserter instrument.
FIG. 6 is a plan view of an alternate embodiment implant engaging portion for the implant inserter instrument of FIG. 5.

In FIG. 5, an implant inserter 140 is provided to facilitate the insertion of an implant in the intervertebral disc space through an access portal. Implant inserter 140 includes an elongate member 142 extending along a longitudinal axis 141. Elongate member 142 is in the form of a rigid, linear shaft having a distal portion 144, a first handle 146 about distal portion 144, and a proximal portion 145 extending proximally from first handle 146. A second handle member 152 between distal shaft portion 144 and proximal portion 145 extends laterally from elongate member 142 along an axis 154. Distal portion 144 includes a length 155 from distal end 147 to the connection of handle member 152 with elongate member 142.

An inner shaft 148 extends through a central passage of elongate member 142. Inner shaft 148 includes a proximal knob 150 and a distal connector 158. Knob 150 can be manually grasped to rotate connector 158 to, for example, threadingly engage an implant thereto. Second handle member 152 is positioned distally of knob 150 to facilitate access thereto. First handle 146 is located proximally of second handle member 152. First handle 146 can be grasped to move the implant distally and axially in the disc space, while second handle member 152 can be grasped to control the lateral positioning and alignment of the implant during insertion. Thus, the surgeon can employ two-handed control to insert the implant to obtain the desired alignment in the disc space.

Implant engaging portion 160 includes a body 161 having a distal end wall 162 from which connector 158 distally projects. A first flange 164 extends distally from body 161 on one side of end wall 162, and a second flange 166 extends distally from body 161 on the opposite side of end wall 162. Second flange 166 includes a projection 168 extending therefrom toward first flange 164. Second flange 166 can include a length greater than that of first flange 164 to facilitate insertion of implants with sidewall cavities or recesses, such as disclosed in U.S. Pat. No. 6,174,311, which is hereby incorporated by reference in its entirety. Furthermore, a slot 170 can be provided to facilitate flexing of second flange 166 relative to body 161 for the engagement of and disengagement of projection 168 with the implant.

An alternative implant engaging portion 180 in FIG. 6 includes a body 181 having a distal end wall 186. A first flange 182 and a second identical flange 184 extend distally from body 181 on opposite sides of end wall 186. A projection 188 can be provided at the distal end of an inner shaft extending through elongate member 142 for engagement with an implant. Flanges 182, 184 prevent the implant from twisting or rotating relative to implant engaging portion 180 when engaged against distal end wall 186 with projection 188. Still other embodiments contemplate an implant engaging portion without distal flanges; an implant engaging portion with two or more clamping members that clamp the implant therebetween; an implant engaging portion the expands to engage an implant receptacle; and other configurations suitable for engaging an implant to the implant inserter.

FIGS. 7-10 illustrate the instruments positioned through a retractor sleeve in a minimally invasive approach to a spinal disc space. In FIGS. 7-10, the retractor sleeve 200 includes a tubular body 206 extending between a distal end 202 and a proximal end 204. A bracket 208 extends from proximal end 202, and is engageable with a flexible arm 210. Flexible arm 210 includes sufficient flexibility for manual bending to allow sleeve 200 to be repositioned in the incision, and includes sufficient stiffness to maintain its repositioning to maintain sleeve 200 in the altered positioning.

In the illustrated embodiment, retractor sleeve 200 is inserted through the skin and tissue to provide a posterior approach offset laterally from the midline of the spinal column. Retractor sleeve can also be positioned for other approaches to the spinal column, including posterior-lateral, lateral, anterior-oblique, anterior, and transforaminal approaches for example. To minimize trauma and disruption to the tissue, the skin and tissue can be sequentially dilated with a plurality of dilators prior to insertion of retractor sleeve 200. After placement of the retractor over the last dilator, the dilators are removed to provide a working channel through retractor sleeve 200 for placement of surgical instruments and implants to the disc space adjacent distal end 204.

Figure 9:
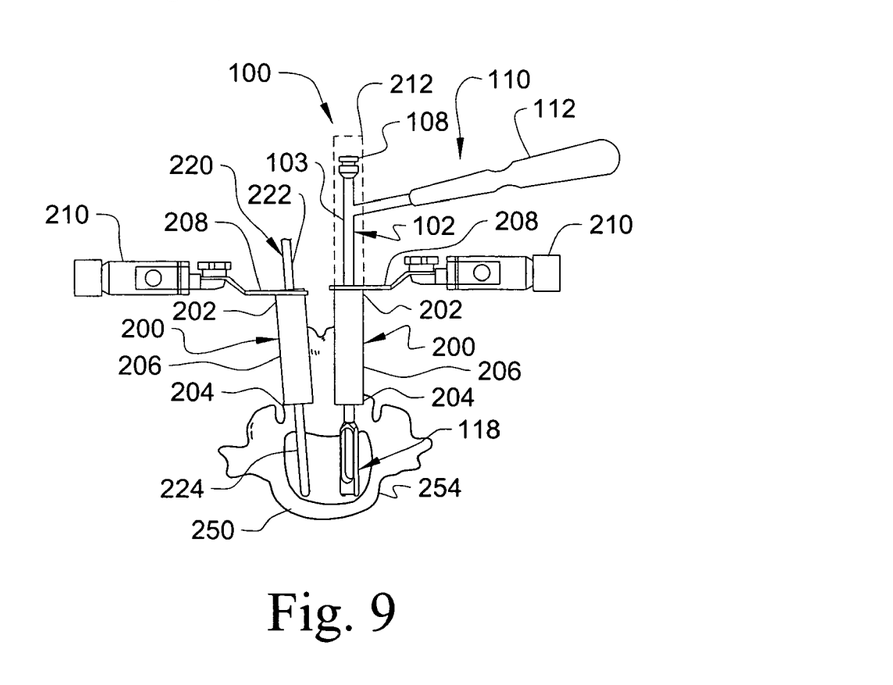
FIG. 9 is a plan view of the chisel instrument of FIG. 4 positioned through a retractor sleeve with the cutting end in a spinal disc space.
Figure 10:
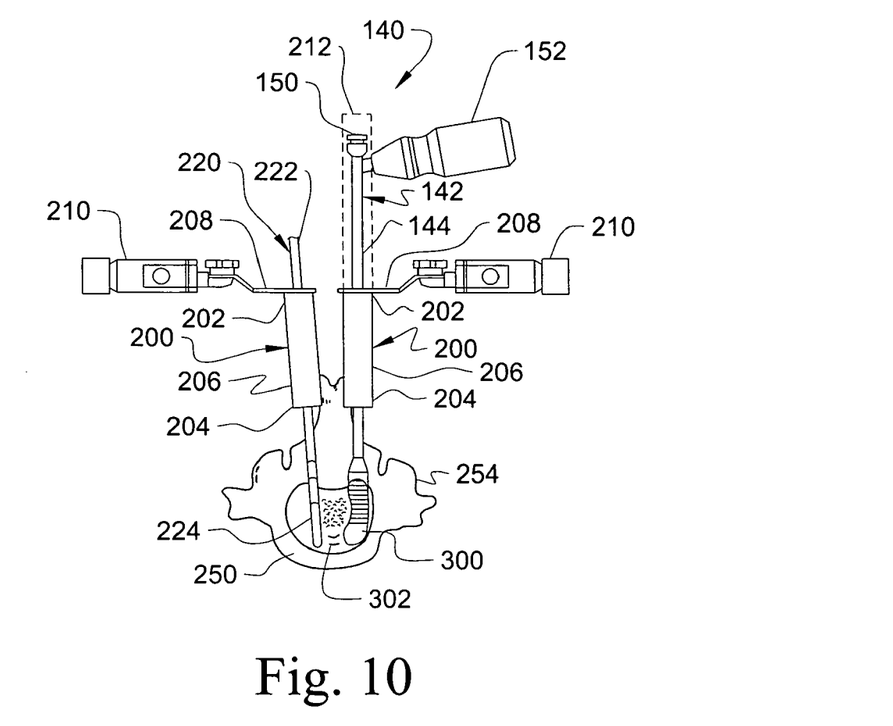
FIG. 10 is a plan view of the implant inserter instrument of FIG. 5 positioned through a retractor sleeve with the implant engaging portion engaged to an implant in a spinal disc space.

It is further contemplated that multiple retractor sleeves can be employed in the same procedure, such as shown in FIGS. 9 and 10. In any event, retractor sleeve 200 can provide a minimally invasive access portal to a spinal disc space 250 between vertebrae 252, 254 that protects the adjacent tissue and anatomical structure from the instruments employed during the procedure. Various viewing systems can be employed during the procedures to visualize the disc space and instruments, including endoscopic viewing elements in retractor sleeve 200 or in a separate portal, microscopic viewing systems, loupes, naked eye, fluoroscopic, CT-scan, X-ray and combinations thereof, for example.

Figure 7:
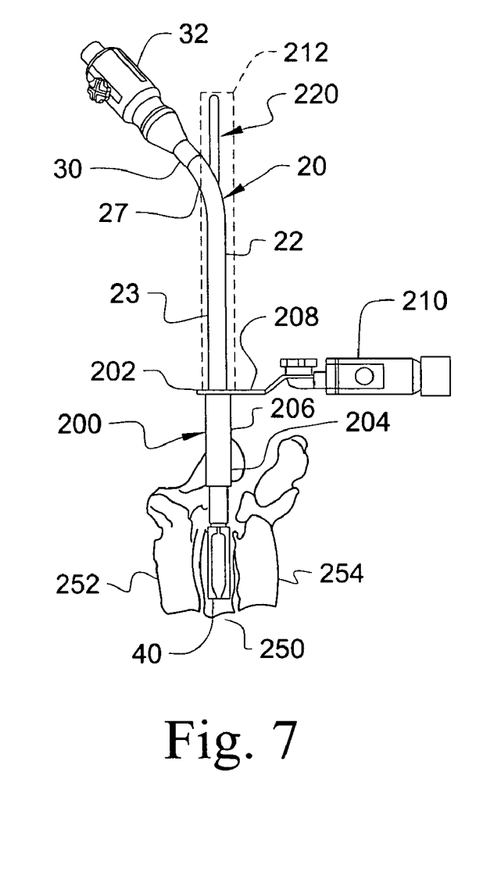
FIG. 7 is a side view of the rotary cutting instrument of FIG. 1 positioned through a retractor sleeve with the cutting end in a spinal disc space.

Referring to FIG. 7, retractor sleeve 200 is positioned through the skin and tissue to provide access to disc space 250. Rotary cutter 20 is positioned through retractor sleeve 200 with cutting element 40 in the disc space to cut and remove disc material and create a channel in the disc material. Distal shaft portion 23 of elongate member 22 includes length 50 sufficient to maintain bend 27 proximally of proximal end 22 during use in disc space 250. Proximal shaft portion 30 is offset by bend 27 to position handle 32 outside a zone 212 defined by a proximal and longitudinal extension of the working channel of retractor sleeve 200. In this configuration, handle 32 is positioned outside zone 212 and out of the operative field of view through the proximal end opening of retractor sleeve 200.

Figure 8:
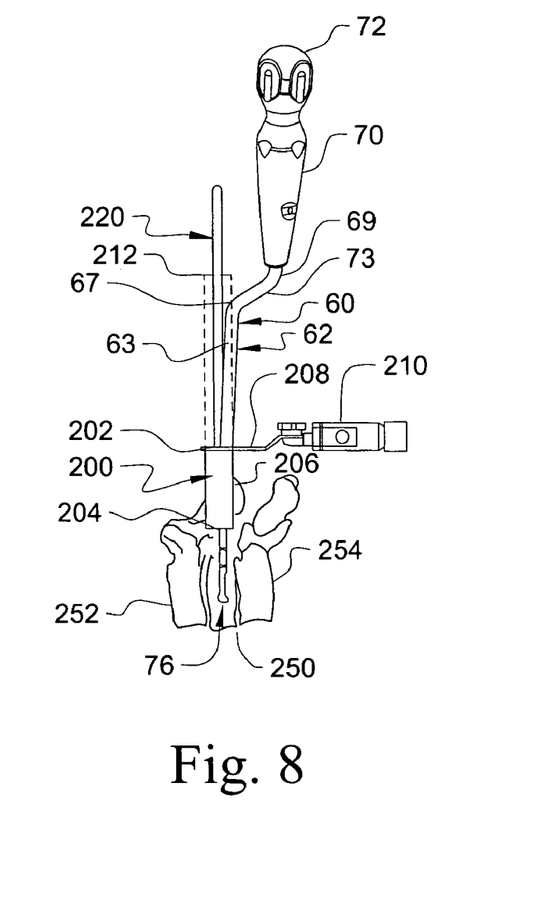
FIG. 8 is a side view of the scraper instrument of FIG. 3 positioned through a retractor sleeve with the cutting end in a spinal disc space.

In FIG. 8, scraper 60 is positioned through retractor sleeve 200 to place scraper head 76 in the disc space where it can be manipulated to cut and remove disc and bone material. Distal portion 63 of elongate member 62 includes length 90 sufficient to maintain offset member 73 proximally of proximal end 212 of retractor sleeve 200 during manipulation of scraper head 76 in disc space 250. Offset member 73 positions handle 70 outside zone 212 and to clear the operative field of view through the proximal end opening of retractor sleeve 200.

In FIG. 9, chisel 100 is positioned through retractor sleeve 200 to place chisel head 118 in the disc space where it can be manipulated to cut a channel or pathway for insertion of an implant. Distal portion 103 of elongate member 102 includes length 134 sufficient to maintain handle member 110 proximally of proximal end 212 of retractor sleeve 200 as chisel head 118 is driven into disc space 250. Handle member 110 is oriented transversely to distal portion 103 so that enlarged handle 112 is positioned outside zone 212 and outside the operative field of view through the proximal end opening of retractor sleeve 200. An impaction force can be delivered to impaction head 108 and transmitted longitudinally along elongate member 102 to chisel head 118 to remove bone material and form an implant insertion path or channel in the vertebral endplates.

In FIG. 9 a second retractor sleeve 200 is shown on the opposite side of the midline of the spinal column. The disc space 250 can be prepared through second retractor sleeve 200 for receipt of a second implant. To provide and maintain distraction of disc space 250 during disc space preparation through first retractor sleeve 200, a distractor 220 is positioned with distracting head 224 in disc space 250. A shaft 222 extends distally from head 224 through the proximal end opening of the second retractor sleeve 200 to facilitate insertion and withdrawal of distractor 220 from disc space 250.

In FIG. 10, an implant 300 is attached to implant inserter 140. Implant 300 is then placed through retractor sleeve 200 and impacted or pushed into the disc space to the desired depth. Distal shaft portion 144 of elongate member 142 includes a length 155 sufficient to maintain handle member 152 proximally of proximal end 212 during insertion of implant 300. Handle member 152 is positioned outside zone 212 to facilitate viewing through the proximal end opening of retractor sleeve 200. Handle member 152 can be manipulated to laterally control the alignment of implant 300 in disc space 250 while a pushing or impaction force is applied axially through elongate member 142. Bone graft 302 or other bone growth material or therapeutic agents can be placed in disc space 250 and/or in implant 300 to promote fusion of the adjacent vertebrae.

The above-described instruments can be employed in for insertion of implants into the intervertebral spaces between adjacent vertebrae. The implants are useful for maintaining and/or restoring a desired spacing between adjacent vertebrae. The implants can be employed in fusion procedures to fuse adjacent vertebrae. It is further contemplated that the implants can be any one or combination of spinal disc replacements; spinal nucleus replacements; flexible or rigid implants; interbody spacer devices that are porous, non-porous, and combinations thereof; interbody spacer devices that include cavities for bone growth therethrough; interbody devices with surface features to promote bone growth and engagement; and implants that include recessed areas that serve as a depot for receiving bone growth material. A single implant or multiple implants can be positioned in the disc space through a single access portal or through multiple access portals.

While the invention has been illustrated and described in detail in the drawings and the foregoing description, the same is considered to be illustrative and not restrictive in character. All changes and modifications that come within the spirit of the invention are desired to be protected.

What is claimed is:

1. A cutting instrument assembly for removal of disc material through a minimally invasive surgical access portal, comprising:
   a rotary cutting instrument, comprising:
      a hollow elongate outer shaft including a distal portion and a proximal portion, said distal portion including a first length between a distal end and a proximal end thereof and extending along a distal longitudinal axis, said proximal portion extending along a proximal longitudinal axis and including an enlarged handle therealong, said distal portion and said proximal portion being connected with a lateral bend with said distal longitudinal axis intersecting said proximal longitudinal axis at an angle between said distal longitudinal axis and said proximal longitudinal axis ranging from 90 degrees to 165 degrees;
      a cutting element rotatably mounted to said distal end of said hollow shaft;
      an inner shaft including a flexible portion connected at a distal end thereof with said cutting element, said flexible portion extending proximally from said distal end through said distal portion and said lateral bend, said inner shaft including a rigid portion in said proximal portion of said outer shaft rotatably mounted in a proximal end opening of said proximal portion, said rigid portion including a tool engaging member at a proximal end thereof spaced proximally from said proximal end of said proximal portion, said tool engaging portion engageable to rotate said inner shaft and said cutting element relative to said outer shaft, wherein said rigid portion of said inner shaft includes a groove extending therearound and said enlarged handle includes a coupling member engaged thereto having a portion positionable into and out of said groove to facilitate disassembly of said inner and outer shafts; and
   a retractor sleeve including a second length extending between a proximal end and a distal end thereof, said first length being greater than said second length, wherein said distal portion of said outer shaft is removably positioned through a working channel of said retractor sleeve with said cutting element spaced distally of said distal end of said retractor sleeve while said lateral bend is spaced proximally from said proximal end of said retractor sleeve.

2. The assembly of claim 1, wherein said angle is 150 degrees.

3. The assembly of claim 1, wherein said cutting element includes a body with a first arm and a second arm spaced from said first arm, said first and second arms extending parallel with said distal longitudinal axis and defining a chamber therebetween.

4. The assembly of claim 3, wherein said first and second arms each include a first cutting blade and an opposite second cutting blade along respective ones of said first and second arms.

5. The assembly of claim 1, wherein said enlarged handle is positioned outside a zone defined by a profile of said working channel extending proximally along a proximal extension of a longitudinal axis of said retractor sleeve when said cutting instrument is positioned through said retractor sleeve.

6. The assembly of claim 1, wherein said cutting element includes a body with a first arm and a second arm spaced from said first arm, said first and second arms each including at least one cutting blade extending along each of upper and lower sides thereof.

7. The assembly of claim 6, wherein said first and second arms extend parallel with said distal longitudinal axis and define a chamber therebetween.

8. The assembly of claim 6, wherein said first and second arms each include opposite convexly curved surfaces extending between said cutting blades thereof.

9. A cutting instrument assembly for removal of disc material through a minimally invasive surgical access portal, comprising:
a rotary cutting instrument, comprising:
a hollow elongate outer shaft including a distal portion and a proximal portion, said distal portion including a first length between a distal end and a proximal end thereof and extending along a distal longitudinal axis, said proximal portion extending along a proximal longitudinal axis, said distal portion and said proximal portion being connected with a lateral bend with said distal longitudinal axis intersecting said proximal longitudinal axis at an angle;
a cutting element rotatably mounted to said distal end of said outer shaft;
an inner shaft connected at a distal end thereof with said cutting element, said inner shaft including at least a flexible portion extending through said lateral bend, said inner shaft including a rigid portion in said proximal portion of said outer shaft rotatably mounted in a proximal end opening of said proximal portion of said outer shaft, said rigid portion including a tool engaging member at a proximal end thereof engageable to rotate said inner shaft and said cutting element relative to said outer shaft, wherein:
said proximal portion of said outer shaft includes an enlarged handle therealong;
said rigid portion of said inner shaft includes a groove extending therearound and said enlarged handle includes a coupling member engaged thereto having a portion positionable into and out of said groove to facilitate disassembly of said inner and outer shafts; and
a retractor sleeve including a second length extending between a proximal end and a distal end thereof, said first length being greater than said second length, wherein said distal portion of said outer shaft is removably positioned through a working channel of said retractor sleeve with said cutting element spaced distally of said distal end of said retractor sleeve while said lateral bend is spaced proximally from said proximal end of said retractor sleeve and said enlarged handle is positioned outside a zone defined by a profile of said working channel extending proximally along a proximal extension of a longitudinal axis of said retractor sleeve when said cutting instrument is positioned through said retractor sleeve.

10. The assembly of claim 9, wherein said angle between said distal longitudinal axis and said proximal longitudinal axis is in the range from 90 degrees to 165degrees 11. The assembly of claim 9, wherein said flexible portion extends from said distal end of said inner shaft to said rigid portion of said inner shaft.

12. The assembly of claim 9, wherein said cutting element includes a body with a first arm and a second arm spaced from said first arm, said first and second arms extending parallel with said distal longitudinal axis and defining a chamber therebetween.

13. A cutting instrument assembly for removal of disc material through a minimally invasive surgical access portal, comprising:
a rotary cutting instrument, comprising:
a hollow elongate outer shaft including a distal portion and a proximal portion, said distal portion including a first length between a distal end and a proximal end thereof and extending along a distal longitudinal axis, said proximal portion extending along a proximal longitudinal axis, said distal portion and said proximal portion being connected with a lateral bend with said distal longitudinal axis intersecting said proximal longitudinal axis at an angle;
a cutting element rotatably mounted to said distal end of said outer shaft;
an inner shaft connected at a distal end thereof with said cutting element, said inner shaft including at least a flexible portion extending through said lateral bend, said inner shaft including a rigid portion in said proximal portion of said outer shaft rotatably mounted in a proximal end opening of said proximal portion of said outer shaft, wherein said rigid portion of said inner shaft includes a groove and said proximal portion of said outer shaft includes a coupling member engaged thereto having a portion positionable into and out of said groove to facilitate disassembly of said inner and outer shafts; and
a retractor sleeve including a second length extending between a proximal end and a distal end thereof said first length being greater than said second length, wherein said distal portion of said outer shaft is positionable through a working channel of said retractor sleeve with said cutting element spaced distally of said distal end of said retractor sleeve and said lateral bend spaced proximally from said proximal end of said retractor sleeve.

14. The assembly of claim 13, wherein said coupling member is engaged to said proximal portion of said outer shaft.

15. The assembly of claim 13, wherein said rigid portion of said inner shaft includes a tool engaging member at a proximal end thereof engageable to rotate said inner shaft and said cutting element relative to said outer shaft.

16. The assembly of claim 13, wherein said groove extends completely around said rigid portion of said inner shaft.

* * * * *

UNITED STATES PATENT AND TRADEMARK OFFICE
CERTIFICATE OF CORRECTION

PATENT NO. : 7,578,820 B2  Page 1 of 1
APPLICATION NO. : 10/653281
DATED : August 25, 2009
INVENTOR(S) : Moore et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1558 days.

Signed and Sealed this

Seventh Day of September, 2010

David J. Kappos
*Director of the United States Patent and Trademark Office*